United States Patent
Meeks

(10) Patent No.: US 7,274,445 B1
(45) Date of Patent: Sep. 25, 2007

(54) CONFOCAL SCATTEROMETER AND METHOD FOR SINGLE-SIDED DETECTION OF PARTICLES AND DEFECTS ON A TRANSPARENT WAFER OR DISK

(75) Inventor: Steven W. Meeks, Fremont, CA (US)

(73) Assignee: KLA-Tencor Technologies Corporation, Milipitas, CA (US)

( * ) Notice: Subject to any disclaimer, the term of this patent is extended or adjusted under 35 U.S.C. 154(b) by 327 days.

(21) Appl. No.: 11/078,462

(22) Filed: Mar. 11, 2005

(51) Int. Cl.
*G01N 21/00* (2006.01)
*G01B 27/40* (2006.01)

(52) U.S. Cl. .............. 356/239.1; 356/236; 356/237.4; 356/237.2; 250/201.3; 250/458.1

(58) Field of Classification Search ..... 356/236–237.4, 356/237.2, 239.1; 250/201.3, 458.1
See application file for complete search history.

(56) References Cited

U.S. PATENT DOCUMENTS 5,629,214 A * 5/1997 Crosby ................. 436/518
6,201,601 B1 * 3/2001 Vaez-Iravani et al. ... 356/237.4
6,597,000 B2 * 7/2003 Stern .................... 250/458.1

* cited by examiner

Primary Examiner—Gregory J. Toatley, Jr.
Assistant Examiner—Iyabo S Alli
(74) Attorney, Agent, or Firm—Caven & Aghevli LLC

(57) ABSTRACT

A problem in the inspection of transparent wafers and disks is the detection of top surface particles. More precisely, it is being able to assign a scattering site as being due to a particle at the top or bottom surface of a transparent wafer. A method of the present invention is to use an elliptical mirror, with a pinhole at its top focus, together with a focused beam. The focused beam will diverge as it passes through the transparent wafer and as a result any particle on the bottom surface will see a lower optical intensity and will appear weaker than a top surface particle. The suppression of scattered light from the bottom surface occurs because the source of the scattered light (the bottom surface) is far from the bottom foci of the elliptical mirror. This means that the light from the bottom surface, which arrives inside the ellipsoid, will be out of focus at the top foci of the ellipsoid and as a result very little light from the bottom surface will pass through the pinhole at the top foci of the elliptical mirror. This reduction of light from the bottom surface can be further improved by making the pinhole diameter to be substantially less than the thickness of the transparent wafer.

23 Claims, 3 Drawing Sheets

CONFOCAL SCATTEROMETER AND METHOD FOR SINGLE-SIDED DETECTION OF PARTICLES AND DEFECTS ON A TRANSPARENT WAFER OR DISK

BACKGROUND OF THE INVENTION

1. Field of the Invention

The present invention generally relates to the field of surface analyzers and more particularly to transparent wafer or disk inspection.

2. Description of Background Art

A problem in the inspection of transparent wafers is the detection of top surface defects without detecting defects from the bottom side of the transparent wafers. Conventional methods for detecting particles (defects) within or upon the top surface of a transparent wafer rely upon illuminating a sample with a beam of light that has been channeled through a modest numerical aperture lens. In these systems, the incident light expands once it leaves the focal point and the intensity of the light decreases as the beam passes through the transparent wafer. The incoming light produces a significant scattering signal when interacting with surface particles and near surface defects on the transparent wafer, while the scattering signal from subsurface and back-surface defects is substantially reduced by the divergence of the incoming beam (reduction in beam intensity). These types of methods are limited to investigation of relatively thick wafers (on the order of 2.0 mm), and the divergence of the beam does not eliminate the signal from the back surface it only reduces it. When analyzing thin transparent wafers with a modest numerical aperture system, the beam which passes through the wafer has sufficient intensity that it becomes difficult to distinguish whether a defect is on the top or bottom of a transparent wafer. Other conventional defect detection systems provide a wavelength of light for illumination that is selected to match an area where the transparent wafer appears opaque, thus minimizing the influence of light scattering from the subsurface or back side of the transparent material. However, many defects are left undetected due to a lack of penetration depth from the incident light. Another problem occurs when transparent wafers have only their top surface polished. The beam which penetrates through the transparent wafer and strikes the bottom (unpolished) surface generates a large scattered light signal. This large scattered light signal from the bottom surface obscures the scattered light from defects on the top surface making top surface defect detection difficult or impossible.

What is needed is a system and method that (1) analyzes transparent wafers using a single sided system, (2) distinguishes the position of scattering sites, (3) measures the effects of scattering only from scattering sites located within an defined depth of the top surface of the wafer, and (4) permits modification of the depth of the scattering sites that are measured.

SUMMARY OF THE INVENTION

The present invention analyzes transparent wafers using a single sided system, distinguishes the position of scattering sites, measures the effects of scattering only from scattering sites located within a defined depth of the top surface of the wafer, and permits modification of the depth of the scattering sites that are measured. An input light beam is focused onto a surface of a transparent wafer. The light penetrates the surface to a scattering depth where the light scatters from a particular scattering site (particle or defect). The scattered light is then collected by an elliptical (or ellipsoidal) mirror and restricted by a pinhole before being channeled into a light sensor for further analysis. The scattering depth is adjusted by varying the diameter of the pinhole to match the depth of focus needed to resolve scattering sites substantially near the top surface of the transparent wafer. The bottom surface of a transparent wafer may also be inspected.

DETAILED DESCRIPTION OF THE INVENTION

An embodiment of the present invention can be described as a confocal scatterometer. A traditional confocal microscope uses the specular return from the sample to form an image. In contrast an embodiment of the invention detects the scattered light return from the sample. The present confocal scatterometer allows for the imaging of defects or particles on top of a transparent surface without interference from the bottom surface. Alternatively, another embodiment may image bottom surface defects or particles without interference from the top surface. In another embodiment, it is possible to image defects within the body of the transparent material by the use of a sufficiently small diameter pinhole and by focusing the ellipsoid to a point within the transparent material.

Figure 1:
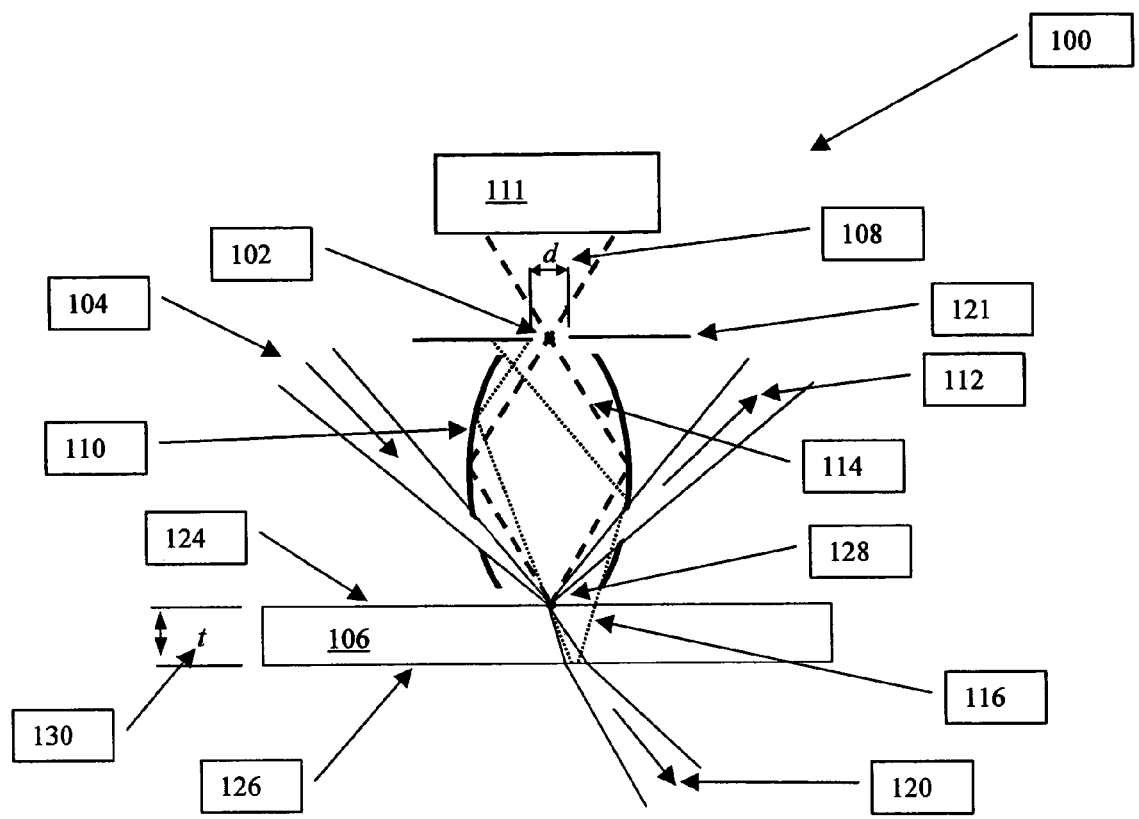
FIG. 1 is an illustration of a system for detecting particles on only the top surface of a transparent surface in accordance with an embodiment of the present invention.

FIG. 1, in accordance with an embodiment of the present invention, illustrates a system 100 for detecting particles on one side of a transparent surface. In an embodiment of the present invention, the transparent surface is a transparent wafer 106 with a top surface 124, a bottom surface 126, and has a thickness "t" 130. The transparent object 106 can be selected from a variety of materials including at least: a semiconducting wafer, a silicon carbide wafer, a sapphire wafer, a lithium niobate wafer, a glass substrate, a lithium tantalate wafer, a gallium nitride wafer, a gallium arsenide wafer or a silicon wafer. An elliptical or ellipsoidal mirror 110, hereafter referred to as an elliptical mirror for convenience, is provided to collect the scattered light from the transparent wafer 106. The ellipsoidal mirror 110 is a body of revolution of an ellipse. In one embodiment, the top and bottom of the ellipsoidal mirror 110 are removed (not shown) and the top focus 102 of the elliptical mirror 110 is positioned within a pinhole 108, of diameter d, within an opaque surface 121 that passes perpendicular to the ellipsoid 110 and contains the top focus 102. The bottom focus 128 of the elliptical mirror 110 is positioned on the top surface 124 of the transparent wafer 106. The optical beam 104 (generated from a 10 microns to 193 nm laser or another optical source) comes to a focus at the bottom focus 128 of the ellipsoid 110 and strikes the top surface 124 of the transparent wafer 106.

When the incoming beam 104 interacts with a scattering site (not shown) on the top surface 124 of the transparent wafer 106, the first scattered beam 114 propagates through elliptical mirror 110. A portion of the incoming beam penetrates the top surface 124 of transparent wafer 106 and a second scattered beam 116 propagates through the elliptical mirror 110 due to interaction with a second scattering site (not shown) at a particular scattering depth. In an embodiment of the present invention (FIG. 1), the second scattering sight is located on the bottom surface 126 of the transparent wafer 106 and the detectable scattering depth is equal to the thickness 130 of the transparent wafer 106. In another embodiment of the present invention (not shown), the second scattering site is located between the top surface 124 and bottom surface 126 of the transparent wafer 106 and the detectable scattering depth is less than the thickness 130 of the transparent wafer 106. The thickness 130 of the transparent wafer 106, according to an embodiment of the present invention, is approximately 250 micrometers.

The first scattered beam 114 is channeled to a focus at a position that is substantially at the top focal point 102 of elliptical mirror 110 in order to pass through the pinhole 108 of opaque surface 121 undisturbed. The first scattered beam 114 is directed onto scatter sensor 111 for further analysis.

Another portion of incoming beam 104 transverses through the top surface 124 and bottom surface 126 of transparent wafer 106 as transmitted beam 120. Another portion of incoming beam 104 transverses through the top surface 124 of transparent wafer 106 and is reflected, as second scattering beam 116, from the bottom surface 126 of the transparent wafer 106. A first portion of second scattering beam 116 propagates through elliptical mirror 110 and is restricted from entering scatter sensor 111 by the diameter d of the pinhole 108 in opaque surface 121. A portion 112 of the incident beam 104 reflects from the top surface of the transparent wafer 124 and exits through an opening in the side of elliptical mirror 110. As shown in U.S. patent application Ser. No. 10/754,275, which is incorporated herein by reference in its entirety, a more detailed analysis of surface particles and defects is available by collecting and analyzing the reflected portion 112 of incident beam 104 with a specular sensor.

According to an embodiment of the present invention, the diameter d of the pinhole 108 in the opaque surface 121 is selected at a value substantially less than the thickness t 130 of the transparent wafer 106. When the diameter d of the pinhole 108 (or two times the depth of focus) is substantially less than the thickness 130 of the transparent wafer 106 and the bottom focus 128 of the elliptical mirror 110 is on the top surface 124, then defects on the top surface 124 are visible in the scattered light detected at scatter sensor 111. Selecting a pinhole diameter up to 70% smaller than the thickness of the transparent wafer is sufficient to distinguish particles on the top and bottom surfaces. For the case that the thickness 130 of the transparent wafer 106 is 250 μm, a pinhole diameter of 150 μm is adequate for distinguishing between top and bottom surface particles. In another embodiment, the diameter d may be chosen to approximately equal the thickness t 130 of the transparent wafer. This embodiment allows the collection of scattered light from both the top 124 and bottom surfaces 126 of the transparent wafer.

The combination of a divergent incoming beam 104 (as it passes through the transparent wafer 106) with an elliptical mirror 110, containing a pinhole 108 positioned at its top focus 102, act to suppress the second scattered light 116 from scattering site(s) on the bottom surface 126 of the transparent wafer 106, sufficiently, to permit only first scattered beam 114 from top surface particles to be detected by scatter sensor 111. The suppression of scattered light from the bottom surface 126 occurs because the source of the scattered light (the bottom surface) is far from the bottom focus 128 of the elliptical mirror 110 as shown in FIG. 1. The second scattered beam 116, representing light scattered from the bottom surface 126, is collected inside the elliptical mirror 110 and it is not focused at the top focus 102 of the elliptical mirror 110 but strikes the opaque surface 121 at a position away from the top focus 102 and, therefore, substantially no scattered light from scattering sites on the bottom surface 126 is allowed to pass through the pinhole which is placed at the top focus of the elliptical mirror 110. Signals reaching scatter sensor 111 are substantially restricted to scattered light from the top surface 124 of the transparent wafer 106. In accordance with another embodiment of the present invention, the amount of light received by scatter sensor 111 from the bottom surface 126 can be further reduced by adjusting the pinhole 108 diameter d to be substantially less than the thickness 130 of the transparent wafer 106.

A substantial amount of the first scattered beam 114 passes through the pinhole 108 since the incoming beam 104 is focused at the bottom focus 128 of the elliptical mirror 110. According to an embodiment, the depth of focus of elliptical mirror 110 can be determined by the diameter of pinhole 108. In particular, for a pinhole of diameter "d" the depth of focus of the mirror will be roughly ±d/2. According to an embodiment of the present invention, a significant rejection of scattering site detection from the bottom surface 126 is accomplished by combining a pinhole 108 that is smaller (preferably much smaller) than the transparent wafer thickness 130 and an incoming beam 104 that is sharply focused. In an embodiment of the present invention, the incoming beam 104 is sharply focused by way of a high numerical aperture. In this manner, the reduction in bottom surface (or near bottom surface) scattering intensity is multiplied, due to the beam divergence and the limited depth of focus of the elliptical mirror 110.

Figure 2:
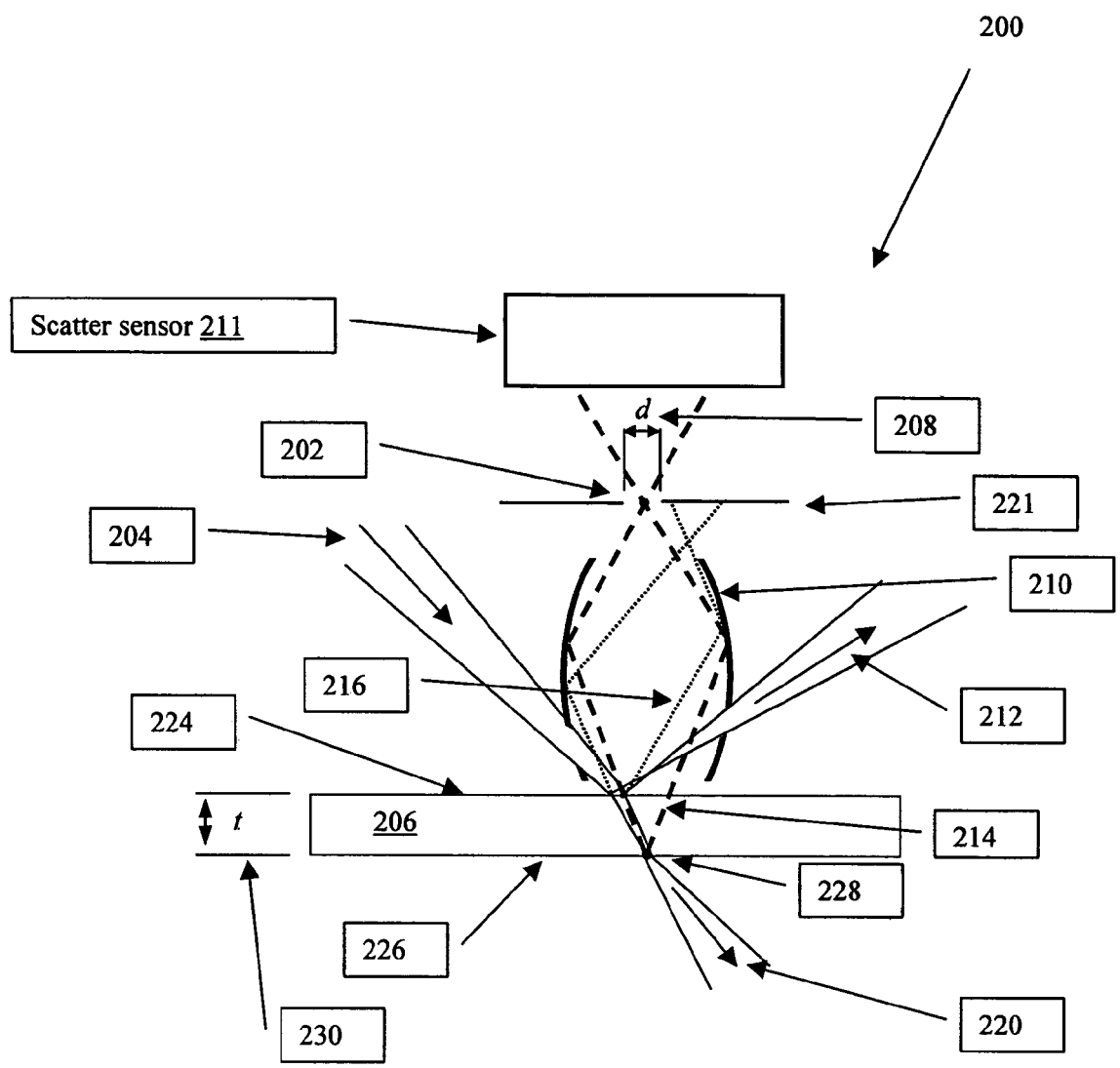
FIG. 2 is an illustration of a system for detecting particles on only the bottom surface of a transparent surface in accordance with an embodiment of the present invention.

FIG. 2 illustrates the case of imaging defects on the bottom surface 226 of the transparent wafer 206 while not detecting defects on the top surface 224 of the transparent wafer 206. The incoming optical beam 204 (from a laser or another optical source) is directed, by adjusting the position of the wafer 206 relative to the ellipsoid 210, so that part of the incoming beam 204 passes through the wafer 206 and comes to a focus which is coincident with the bottom focus 228 of the elliptical mirror 210 which is now located at the bottom surface 226 of the wafer. Another portion, second scattered beam 216, of incoming beam 204 reflects from the top surface 224 of transparent wafer 206 and is blocked by the opaque surface 221. Yet another portion 220 of incoming optical beam 204 passes completely through the top 224 and bottom 226 surface of transparent surface 206. A first portion 212 of incident beam 204 reflects from the top surface 224 and escapes through a hole in the side of the elliptical mirror 210.

First scattered light 214 from the bottom surface 226 of transparent wafer 206 reflects from the elliptical mirror 210 and is directed to the top focus 202 of the mirror 210 where it passes through the pinhole 208 and is directed to a scattered light sensor 211. The scattered light sensor 211 may be a photo multiplier tube, an avalanche photodiode or a PIN photodiode. Second scattered light beam 216, from the top surface 224 of the wafer 206, reflects from the elliptical mirror 210 in a manner that it does not pass through the pinhole 208. The pinhole 208 is a circular or non-circular hole of diameter d in an opaque surface 221 that is placed in a plane perpendicular to the plane of the mirror and contains the top focus 202 of the elliptical mirror 210. The smaller the diameter d of the pinhole 208, the narrower (in the thickness 230 direction) is the depth over which scattered light will be detected. In the case of a pinhole which is approximately the same diameter as the focused beam, the thickness range over which scattered light is detected is roughly half the diameter of the pinhole. If, for example, the focused laser beam (as well as the pin hole) is 1 micron in diameter then the scattered light will be collected from a thickness range of +−5000 Angstroms about the bottom focal point of the ellipsoid. This can be estimated by assuming a pair of light rays 214 incident at 45° upon a pinhole of diameter d. These rays cross one another at the top focus 202 of the elliptical mirror 210 and they will expand to a diameter d when they have moved a distance ±d/2 from the top focal point 202. This means that scattered light emanating from points, which are more than ±d/2 above or below the bottom focus 228 of the elliptical mirror, do not entirely pass through the pinhole and experience substantial attenuation.

Another embodiment of the present invention inspects both sides of a transparent wafer, with access to a single side at a time. That is, it is possible to locate optical body 100 or 200 above the top surface of a transparent wafer and to scan the top surface 124 for defects using the configuration shown in FIG. 1 and to scan the bottom surface 226 using the configuration shown in FIG. 2. The inspection of the top surface may be done serially by first scanning the top surface 124 (FIG. 1) at bottom focus 128 and then moving the bottom focus 228 down to the bottom surface 226 for scanning the bottom surface 226 (FIG. 2).

In another embodiment, when using a sufficiently small pinhole, it is possible to image internal cross sectional planes that lay within the bulk of the transparent wafer without interference from either the top or bottom surfaces. This can be enhanced by using P polarized light and operating at an angle of incidence that is near the Brewster's angle for the particular material that is being examined. This embodiment allows a maximum amount of light to penetrate through the substrate and therefore a maximum amount of energy is available to image internal defects within the bulk of the transparent wafer. P scattered light also optimizes the amount of scattered light from small particles.

Figure 3:
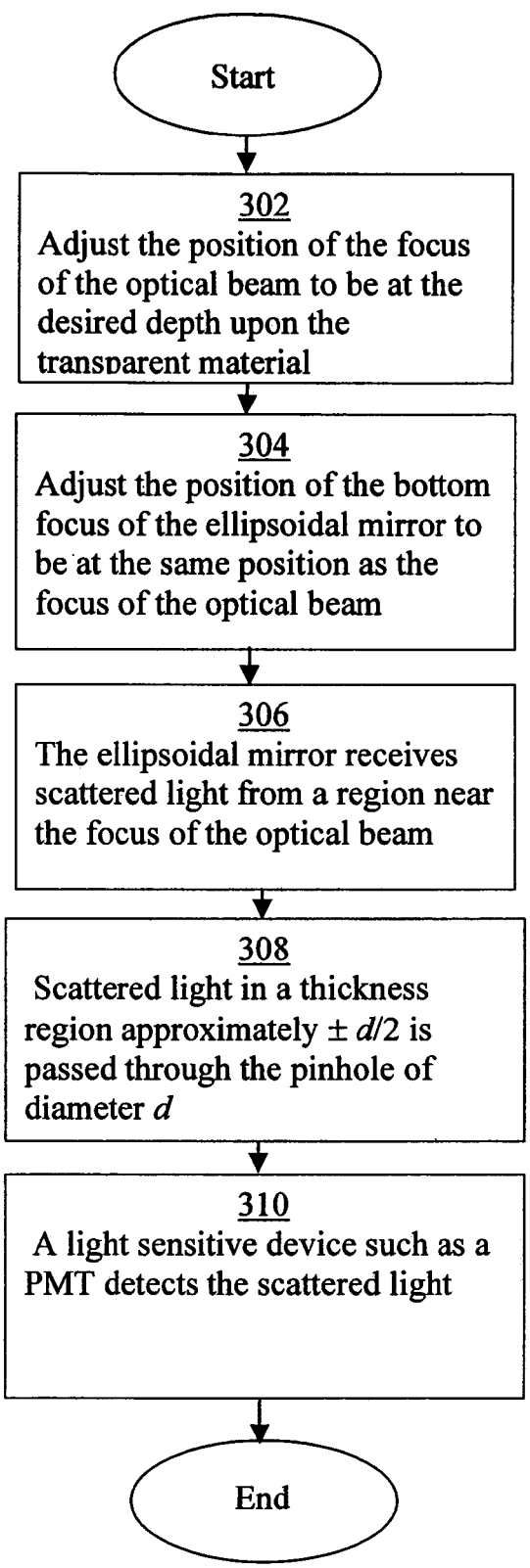
FIG. 3 is a flowchart illustrating a method for detecting particles on only one side of a transparent surface in accordance with an embodiment of the present invention.

FIG. 3 illustrates a method for detecting particles or defects on the top, bottom or within the bulk of a transparent wafer or disk. First the position of the focus of the optical beam is adjusted 302 to be at the desired depth upon the transparent material. Then the position of the bottom focus of the elliptical mirror is adjusted 304 to be at the same position as the focus of the optical beam. The elliptical mirror receives 306 the scattered light from a region near the focus of the optical beam. The scattered light in a thickness region approximately ±d/2 is passed 308 through the pinhole of diameter d. A light sensitive device such as a PMT receives and detects 310 the scattered light.

Many technologically important materials are opaque in the visible light region (400 to 700 mn). However, many of these materials may be transparent at longer or shorter wavelengths. For example, Silicon is opaque to visible light but becomes transparent at wavelengths longer than 1.1 microns. Thus if Silicon is imaged with, for example 1.55 micron light it will be transparent and all the ideas discussed above may be applied to the inspection of Silicon wafers. Similar ideas may be applied to GaAs except even longer wavelengths would be required to make GaAs transparent.

While the invention has been particularly shown and described with reference to a preferred embodiment and various alternate embodiments, it will be understood by persons skilled in the relevant art that various changes in form and details can be made therein without departing from the spirit and scope of the invention.

The invention claimed is:

1. A system for detecting a scattering site in a transparent object having a thickness less than 350 micrometers, the system comprising:
    a radiation source to direct radiation toward a surface of the transparent object at an oblique angle;
    a mirror having a substantially ellipsoid shape, having a first foci and a second foci, said second foci positioned substantially at a first position of the transparent object;
    an opaque surface having a pinhole positioned substantially at said first foci, said pinhole having a first diameter corresponding to a first depth of focus of said elliptical mirror, for permitting a first scattering signal to pass through said pinhole that is scattered from the scattering site within said first depth of focus, wherein said pinhole diameter is less than or equal to the thickness of the object; and
    a sensor for receiving said first scattering signal.

2. The system of claim 1 wherein said first position is at a top surface of the transparent object.

3. The system of claim 1 wherein said first position is at a bottom surface of the transparent object.

4. The system of claim 1 wherein said first position is within the transparent object.

5. The system of claim 1, wherein the transparent object is a semiconducting wafer, a silicon carbide wafer, a sapphire wafer, a lithium niobate wafer, a lithium tantalate wafer, a gallium nitride wafer, a gallium arsenide wafer or a silicon wafer.

6. The system of claim 1, wherein the sensor is a photoconductor.

7. The system of claim 1, wherein the sensor is a photomultiplier tube or an avalanche photodiode, or a PIN photodiode.

8. The system of claim 1, wherein said pinhole diameter is 175 micrometers.

9. The system of claim 1, wherein said pinhole diameter is 100 micrometers.

10. A method for detecting a particle near a first position of a transparent object, having a thickness less than 350 microns, with an elliptical mirror, having an opaque surface with a pinhole, at a first foci of the elliptical mirror, wherein the pinhole diameter is less than or equal to the thickness of the object, the method comprising the steps of:
    directing radiation from a radiation source toward a surface of the transparent object at an oblique angle;
    permitting a first scattering signal to pass through the pinhole, said first scattering signal is scattered from a first scattering site located near the first position of the transparent object, within a first depth of focus of the elliptical mirror, said first depth of focus proportional to the first diameter;
    receiving said first scattering signal with a scattering sensor; and
    detecting the particle in said first scattering site.

11. The method of claim 10 wherein said first position is at a top surface of the transparent object.

12. The method of claim 10 wherein said first position is at a bottom surface of the transparent object.

13. The method of claim 10 wherein said first position is within the transparent object.

14. The method of claim 10, wherein said first depth of focus is 175 micrometers.

15. The method of claim 10, wherein said first depth of focus is 100 micrometers.

16. The method of claim 10, wherein the transparent object is a semiconducting wafer, a silicon carbide wafer, a sapphire wafer, a lithium niobate wafer, a lithium tantalate wafer, a gallium nitride wafer, a gallium arsenide wafer or a silicon wafer.

17. The method of claim 10, wherein the sensor is a photoconductor.

18. The method of claim 10, wherein the sensor is a photomultiplier tube or an avalanche photodiode, or a PIN photodiode.

19. The system of claim 1, wherein said pinhole diameter is less than 100 micrometers.

20. The method of claim 10, wherein said first depth of focus is less than 100 micrometers.

21. The system of claim 1, wherein a diameter of the pinhole is approximately 70% smaller than the thickness of the object.

22. The system of claim 1, wherein the mirror has a depth of focus approximately equal to half the diameter of the pinhole.

23. The system of claim 1, wherein the mirror comprises:
a first aperture to permit radiation from the radiation source to access a service of the wafer; and
a second aperture to permit a portion of the radiation reflected from the surface of the wafer to exit the mirror.

* * * * *